US005705606A

United States Patent [19]
Charo et al.

[11] Patent Number: 5,705,606
[45] Date of Patent: Jan. 6, 1998

[54] PEPTIDES DERIVED FROM GPIIIA

[75] Inventors: Israel F. Charo, Lafayette; Laurence A. Fitzgerald, San Mateo; David R. Phillips, Oakland, all of Calif.

[73] Assignee: COR Therapeutics, Inc., So. San Francisco, Calif.

[21] Appl. No.: 170,596

[22] Filed: Dec. 21, 1993

Related U.S. Application Data

[63] Continuation of Ser. No. 819,604, Jan. 9, 1992, abandoned, which is a continuation of Ser. No. 640,567, Jan. 14, 1991, abandoned, which is a continuation of Ser. No. 336,962, Apr. 12, 1989, abandoned, which is a continuation-in-part of Ser. No. 213,641, Jun. 30, 1988, abandoned.

[51] Int. Cl.$^6$ .................... C07K 14/705; C07K 14/75; C07K 14/47; A61K 38/16
[52] U.S. Cl. .................... 530/300; 514/2; 514/12; 514/13; 514/14; 530/324; 530/327; 530/350; 530/395; 530/326; 530/325; 530/345; 530/402; 530/403; 530/806; 424/184.1; 424/185.1; 424/193.1; 424/195.11; 424/198.1
[58] Field of Search .................... 514/2, 12, 13, 514/14; 530/300, 324, 327, 350, 395, 326, 325, 345, 402, 403, 806; 424/184.1, 185.1, 193.1, 195.11, 198.1

[56] References Cited

U.S. PATENT DOCUMENTS

| | | | |
|---|---|---|---|
| 4,578,079 | 3/1986 | Ruoslahti et al. | 623/11 |
| 4,766,073 | 8/1988 | Murray et al. | 435/172.3 |
| 4,889,919 | 12/1989 | Murray et al. | 530/351 |
| 5,149,780 | 9/1992 | Plow et al. | 530/324 |

FOREIGN PATENT DOCUMENTS

| | | |
|---|---|---|
| 0 177 957 | 4/1986 | European Pat. Off. . |
| 0 259 632 | 3/1988 | European Pat. Off. . |
| 0 288 307 | 10/1988 | European Pat. Off. . |
| 0 325 224 | 7/1989 | European Pat. Off. . |
| 9307169 | 4/1993 | WIPO . |

OTHER PUBLICATIONS

R. Pytela, M.D. Pierschbacher, M.H. Ginsberg, E.F. Plow, E. Ruoslahti, *Science* (1986), 231:1559, Platelet membrane glycoprotein I Ib/IIIa: Member of a family of Arg-Gly-Asp-specific adhesion receptors.

E.F. Plow, A.H. Srouji, D. Meyer, G. Marguerie, M.H. Ginsberg, *J. Biol. Chem.* (1984), 259:5388, Evidence that three adhesive proteins interact with a common recognition site on activated platelets.

M.D. Pierschbacher, E.G. Hagman, E. Ruoslahti, *Cell* (1981), 26:259, Location of the cell attachment and proteolytic fragments of the molecule.

M.D. Pierschbacher, E. Ruoslahti, *Nature* (1984), 309:30, Cell attachment activity of fibronectin can be duplicated by small synthetic fragments of the molecule.

K.M. Yamada, D.W. Kennedy, *J. Cell Biol* (1984) 99:29, Dualistic nature of adhesive protein function: Fibronectin and its biologically active peptide fragments can autoinhibit fibronectin function.

E. Ruoslahti, M.D. Pierschbacher, *Science* (1987), 238:491, New perspectives in cell adhesion: RGD and integrins.

M.E. Humphries, K. Olden, K.M. Yamada, *Science* (1986) 233:467, A synthetic peptide from fibronectin inhibits experimental metastasis of murine melanoma cells.

E.F. Plow, M.D. Pierschbacher, E. Ruoslahti, G. Marguerie, M.H. Ginsberg, *Proc. Natl. Acad. Sci USA* (1985), 82:8057, The effect of Arg–Gly–Asp-containing peptides on fibrinogen and von Willebrand factor binding to platelets.

S. Timmons, M. Kloczewiak, J. Hawiger, *Proc. Natl. Acad. Sci USA* (1984) 81:4935, ADP–dependent common receptor mechanism for binding of von Willebrand factor and fibrinogen to human platelets.

S.C. Lam, E.F. Plow, M.A. Smith, A. Andrieux, J-J Ryckwaert, G. Marguerie, M.H. Ginsberg, *J. Biol. Chem.* (1987) 262:947, Evidence that Arginyl–Glycyl–Aspartate peptides and fibrinogen γ chain peptides share a common binding site on platelets.

M. Ginsberg, M.D. Pierschbacher, E. Ruoslahti, G. Marguerie, E.F. Plow, *J. Biol. Chem.* (1985) 260:3931, Inhibition of fibronectin binding to platelets by proteolytic fragments and synthetic peptides which support fibroblast adhesion.

T. K. Gartner and J. S. Bennett, *J. Biol. Chem.* (1985), 260:11891–11894, The tetrapeptide analogue of the cell attachment site of fibronectin inhibits platelet aggragation and fibrinogen binding to activated platelets.

D. Phillips, I. Charo, L. Parise, and L. Fitzgerald, *Blood* (1988), 71:831–843, The platelet membrane glycoprotein IIb–IIIa complex.

J. Calvete, G. Rivas, M. Maruri, M. Alvarez, J. McGregor, C. Hew, and J. Gonzalez–Rodriguez, *J. Biol. Chem.* (1988), 250:697–704, Tryptic digestion of human GPIIIa.

I. Charo, L. Bekeart, and D. Phillips, *J. Biol. Chem.* (1987), 262:9935–9938, Platelet glycoprotein IIb–IIIa–like proteins mediate endothelial cell attachments to adhesive proteins and the extracellular matrix.

L. Parise, S. Helgerson, B. Steiner, L. Nannizzi, and D. Phillips, *J. Biol. Chem.* (1987), 262:12597–12602, Synthetic peptides derived from fibrinogen and fibronectin change the conformation of purified platelet glycoprotein IIb–IIIa.

A. Nurden, J. George, and D. Phillips, *Biochemistry of Platelets* (1986), Academic Press, pp. 159–223, Platelet membrane glycoproteins: Their structure, function, and modification in disease.

L. Fitzgerald, B. Steiner, S. Rall, Jr., S. Lo, and D. Phillips, *J. Biol. Chem.* (1987), 262:3936–3939, Protein sequence of endothelial glycoprotein IIIa derived from a cDNA clone.

(List continued on next page.)

*Primary Examiner*—Ronald B. Schwadron
*Attorney, Agent, or Firm*—Townsend and Townsend and Crew, LLP

[57] ABSTRACT

The present invention provides oligopeptides corresponding to regions of the GPIIIa protein, which are capable of specifically binding aggregation mediators, such as fibrinogen. The oligopeptides will typically comprise at least about 5 to 20 amino acids, and are thus non-immunogenic and easy to produce, formulate and administer.

6 Claims, No Drawings

OTHER PUBLICATIONS

M. Koczewiak, S. Timmons, T. Lukas, and J. Hawiger, *Biochemistry* (1984), 23:1767, Platelet receptor recognition site on human fibrinogen. Synthesis and structure–function relationship of peptides corresponding to the carboxy–terminal segment of the γ chain.

A. Hiraiwa, A. Matsukage, H. Shiku, T. Takahashi, K. Naito, and K. Yamada. *Blood* (1987), 69:560–564, Purification and partial amino acid sequence of human platelet membrane glycoproteins IIb and IIIa.

D. Haverstick, J. Cowan, K. Yamada, and S. A. Santoro, *Blood* (1985), 66:946–952, Inhibition of platelet adhesion to fibronectin, fibrinogen and von Willebrand factor substrates by a synthetic tetrapeptide derived fo rm the cell–binding domain of fibronectin.

R. Dalla Favera, E.P. Gelmann, R.C. Gallo and F. Wong–Staal, *Nature* (Jul. 2, 1981) 292:31–35, A human onc gene homologous to the transforming gene (v–sis) of a simian sarcoma virus.

S.G. Devare, E. P. Reddy, K.C. Robbins, P.R. Andersen, S. R. Tronick and S. A. Aaronson, *Proc. Natl. Acad. Sci. USA* (May 1982) 79:3179–3182, Nucleotide sequence of the transforming gene of simian sarcoma virus.

K. Glenn, D. F. Bowen–Pope, and Russell Ross, *J. Biol. Chem.* (May 10, 1982) 257:5172–5176, Platelet–derived growth factor. III. Identification of a platelet–derived growth factor receptor by affinity labeling.

S.F. Josephs, R.D. Favera, E.P. Gelmann, R.C. Gallo, F. Wong–Staal, *Science* (1983) 219:503–505, 5' viral and human cellular sequence corresponding to the transforming gene of simian sarcoma virus.

H. N. Antoniades and M. W. Hunkapiller, *Science* (1983) 220:963–965, Human platelet derived growth factor (PDGF): Amino–terminal amino acid sequence.

M. Waterfield, G.T. Scrace, N. Whittle, P. Stoobant, A. Johnsson, A. Wateson, B. Westermark, C.H. Heldin, J.S. Huang and T. F. Deuel, *Nature* (Jul. 7, 1983) 304:35–39, Platelet–derived growth factor is structurally related to the putative transforming protein p28$^{sis}$ of simian sarcoma virus.

R.F. Doolittle, et al., *Science* (Jul. 15, 1983) 221:275–276, Simian sarcoma virus onc gene, v–sis is derived from the gene (or genes) encoding a platelet–derived growth factor.

T.F. Deuel, J. S. Huang, S.S. Huang, P. Stroobant, M.D. Waterfield, *Science* (1983) 221:1348–1350, Expression of a platelet–derived growth factor–like protein in simian sarcoma virus transformed cells.

K.C. Robbins, H.N. Antoniades, S.G. Devare, M.W. Hunkapiller and S.A. Aaronson, (Oct. 13, 1983) *Nature* 305:605–608, Structural and immunological similarities between simian sarcoma virus gene product(s) and human platelet–derived growth factor.

S.F. Josephs, C. Guo, L. Ratner, F. Wong–Staal, (Feb. 3, 1984) *Science* 223:487–491, Human protooncogene nucleotide sequences corresponding to the transforming region of simian sarcoma virus.

S.F. Josephs, L. Ratner, M.F. Clarke, E.H. Westin, M.S. Reitz, F. Wong–Staal, *Science* (1984) 225:636–639, Transforming potential of human c–sis nucleotide sequences encoding platelet–derived growth factor.

C. Betsholz, A. Johnsson, C.H. Heldin, B. Westermark, P. Lind, M.S. Urdea, R. Eddy, T.B. Shows, K. Philpott, A.L. Mellor, T.J. Knott and J. Scott, *Nature* (1986) 320:695–699, cDNA sequence and chromosomal localization of human platelet–derived growth factor A–chain and its expression in tumor cell lines.

I. Charo, L. Fitzgerald, B. Steiner, S. Rall, L. Bekeart and D. Phillips, *Proc. Natl. Acad. Sci. USA* (1986) 83:8351–8355, Platelet glycoproteins IIb and IIIa: Evidence for a family of immunologically and structurally related glycoproteins in mammalian cells.

E. Plow, J. Loftus, E. Levin, D. Fair, D. Dixon, J. Forsyth and M. Ginsberg, *Proc. Natl. Acad. Sci. USA* (1986) 83:6002–6006, Immunologic relationship between platelet membrane glycoprotein GPIIb/IIIa and cell surface molecules expressed by a variety of cells.

C. Cierniewski, S. Niewiarowski, D. Hershock, B. Rucinski and A. Schmaier, *Biochim. Biophys. Acta* (1987) 924:216–224, Quantitation and characterization of human platelet glycoprotein IIIa by radioimmunoassay.

Merck Manual, 11th ed. (1966) p. 1318.

Foon, Cancer Res., 49: 1621–39, 1989.

Edgington, Bio/Technology, 10: 383–386, 388, 389, 1992.

Charo et al., J. Biol Chem., 266:1415–21, 1991.

PEPTIDES DERIVED FROM GPIIIA

This is a continuation of application Ser. No. 07/819,604, filed Jan. 9, 1992, now abandoned, which is a continuation of application Ser. No. 07/640,567, filed Jan. 14, 1991, now abandoned, which is a continuation of application Ser. No. 07/336,962, filed Apr. 12, 1989, now abandoned, which is a continuation-in-part of application Ser. No. 07/213,641, filed Jun. 30, 1988, now abandoned.

FIELD OF THE INVENTION

The present invention relates generally to novel research, diagnostic and therapeutic agents and, more particularly, to compositions and methods useful, e.g., in the prevention and treatment of platelet-associated ischemic disorders.

BACKGROUND OF THE INVENTION

Heart disease is the primary cause of death in most western societies. The most prevalent heart disease states are related to platelet-dependent ischemic syndromes, including, but not limited to, atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, anastomosis of vascular grafts, and chronic cardiovascular devices (e.g., in-dwelling catheters). These syndromes represent a variety of stenotic and occlusive vascular disorders thought to be initiated by platelet activation on vessel walls.

Circulating platelets have been shown to play a central role in the blood vessel response to injuries, such as narrowing, plaque, foreign body presence (e.g., catheters) and the like. Very briefly, endothelial cell injury leads to a sequence of events including platelet adherence, platelet aggregation, and formation of microthrombi; and ultimate release of platelet granular components, including potent cellular mitogenic factors. These components assist in hemostasis, but can also induce undesirable events. Clinical manifestations of platelet related diseases can include any variety of atherosclerotic or separately, thrombotic phenomenon.

Unfortunately, presently available therapeutic agents have not been proven to be of significant value in the broad treatment of platelet-associated ischemic disorders. Recently, attempts to inhibit thrombus formation have focused on blocking platelet adherence or aggregation. For example, short peptide sequences derived from both fibronectin and fibrinogen have been shown to inhibit platelet aggregation. These peptides are unlikely to be of therapeutic value, however, since adhesion of other cells (e.g., endothelial cells to the extracellular matrix) is also disrupted in their presence.

Other research has focused on blocking platelet aggregation at a crucial step in platelet recruitment i.e., fibrinogen binding. Mouse monoclonal antibodies against the fibrinogen receptor on platelets have been shown to reduce platelet aggregation in certain animal studies, but these are highly immunogenic, due to their size and foreign origin.

Thus, novel therapeutic treatment regimens for preventing or least mitigating undesirable thrombus formation are needed. In particular, therapeutic agents capable of blocking or inhibiting thrombus formation at specific locations would provide major therapeutic benefits.

Ideally, these agents will be potent, yet non-immunogenic to most patients. Also, the agent should be easy to administer, yet stable and economical to produce. Further, these agents should act transiently and be capable of functioning at the earliest stages of thrombus formation, without interfering with long-term hemostasis. The present invention fills these and other related needs.

SUMMARY OF THE INVENTION

Novel methods and compositions are provided for inhibiting platelet aggregation and other activities utilizing oligopeptides capable of specifically binding aggregation mediators, such as fibrinogen. The oligopeptides will typically comprise at least about five to twenty amino acids, and are thus non-immunogenic and easy to produce, formulate and administer. These oligopeptides will be useful in treating a variety of platelet-related diseases.

DESCRIPTION OF THE SPECIFIC EMBODIMENTS

The present invention provides novel compositions and methods for treating platelet-associated ischemic syndromes by preventing or substantially inhibiting the formation of platelet aggregates. More specifically, oligopeptides mimicking regions of the receptor for platelet mediators, such as fibrinogen, are utilized to interfere with aggregation. In this regard, the term "blocking oligopeptide" indicates a peptide capable of binding to platelet mediators and interfering with activity of mediator receptors, particularly the receptors on stimulated platelets that bind fibrinogen, fibronectin and von Willebrand factor. These receptors are primarily responsible for recognition (i.e., binding) of the mediators and inducing their activities. The peptides can also act to impede the conversion of fibrinogen to fibrin for use in platelet or whole blood storage, and have a variety of other utilities, including as an immunogen to raise antibodies against the receptor.

The blocking oligopeptides can be used individually or together for the treatment regimens. Depending upon the particular use, the peptides may be labelled or unlabelled, conjugated to carriers, admixed with other compounds, or the like.

Typically, the peptides of interest will be derived from the amino-terminal portion of the platelet membrane glycoprotein (GP) IIIa, which is known to form a $Ca^{2+}$-dependent heterodimer complex with GPIIb (see, Phillips, et al., *Blood*, 71:831–843 (1988), which is incorporated herein by reference). This GPIIb/IIIa complex constitutes, inter alia, the fibrinogen and fibrinonectin receptor on stimulated platelets. A biochemically and immunologically similar membrane glycoprotein complex has been shown to be present on endothelial cells as well.

Preferably, the peptides will comprise contiguous stretches within the first 200 amino-terminal residues of GPIIIa as shown in Table 1 (see, Fitzgerald, et al., *J. Biol. Chem.*, 262:3936–3939 (1987), which is incorporated herein by reference). Table 2 presents ten of the most preferred peptides of the present invention, each of which may include additional natively-associated amino acids (i.e., from the naturally-occurring GPIIIa sequence) or other additional components.

TABLE 1

| 1  | G | P | N | I | C | T | T | R | G | V | 10 |
|----|---|---|---|---|---|---|---|---|---|---|----|
| 11 | S | S | C | Q | C | C | L | A | V | S | 20 |
| 21 | P | M | C | A | W | C | S | D | E | A | 30 |
| 31 | L | P | L | G | S | P | R | C | D | L | 40 |

TABLE 1-continued

| 41 | K | E | N | L | L | K | D | N | C | A | 50 |
|---|---|---|---|---|---|---|---|---|---|---|---|
| 51 | P | E | S | I | E | F | P | V | S | E | 60 |
| 61 | A | R | V | L | E | D | R | P | L | S | 60 |
| 71 | D | K | G | S | G | D | S | S | Q | V | 70 |
| 81 | T | Q | V | S | P | Q | R | I | A | L | 80 |
| 91 | R | L | R | P | D | D | S | K | N | F | 90 |
| 101 | S | Y | Q | V | R | Q | V | E | D | Y | 110 |
| 111 | P | V | D | I | Y | Y | L | M | D | L | 120 |
| 121 | S | Y | S | M | K | D | D | L | W | S | 130 |
| 131 | I | Q | N | L | G | T | K | L | A | T | 140 |
| 141 | Q | M | R | K | L | T | S | N | L | R | 150 |
| 151 | I | G | F | G | A | F | V | D | K | P | 160 |
| 161 | V | S | P | Y | M | Y | I | S | P | P | 170 |
| 171 | E | A | L | E | N | P | C | Y | D | M | 180 |
| 181 | K | T | T | C | L | P | M | F | G | Y | 190 |
| 191 | K | H | V | L | T | L | T | D | Q | V | 200 |

(SEQ ID NO:15)

TABLE 2

| I | G S P R C D L K E N L L K D N C A P | (SEQ ID NO:1) |
|---|---|---|
| II | A R V L E D R P L S D K G S G D S S Q V | (SEQ ID NO:2) |
| III | R L R P D D S K N F S | (SEQ ID NO:3) |
| IV | Q V R Q V E D Y P V D | (SEQ ID NO:4) |
| V | S Y S M K D D L W S | (SEQ ID NO:5) |
| VI | A T Q M R K L T | (SEQ ID NO:6) |
| VII | Y I S P P E A L E N P C Y D M K T T | (SEQ ID NO:7) |
| VIII | D Q V T R F N E E V K K Q S V S R N R D | (SEQ ID NO:8) |
| IX | E E V K K Q S V S R N R D A P E G G F D | (SEQ ID NO:9) |
| X | V C D E K I G W R N D A S | (SEQ ID NO:10) |

Single Letter Code for Amino Acids

| A-Alanine | G-Glycine | M-Methionine | S-Serine |
|---|---|---|---|
| C-Cysteine | H-Histidine | N-Asparagine | T-Threonine |
| D-Aspartic Acid | I-Isoleucine | P-Proline | V-Valine |
| E-Glutamate | K-Lysine | Q-Glutamine | W-Tryptophan |
| F-Phenylalanine | L-Leucine | R-Arginine | Y-Tyrosine |

Most preferably, the peptides will comprise at least a portion of peptide IX, so long as the peptide maintains the desired properties (e.g., fibrinogen binding, mimicking the fibrinogen binding site on GPIIIa, suitable for presenting antigenic determinant for raising antibodies against GPIIIa, and the like). For example, additional suitable peptides are derived from GPIIIa amino-terminal residues between about 203 and about 227, as follows:

203-227

N E E V K K Q S V S R N R D A P E G G F D A I M Q A
(SEQ ID NO.:11)

XXIII

N E E V K K Q S V S R N R D A P E G G (SEQ ID NO.:12)

XXIV

S V S R N R D A P E G G F D A I M Q A (SEQ ID NO.:13)

XXIII/XXIV (Overlap)

S V S R N R D A P E G G (SEQ ID NO.:14)

The peptides of interest will include at least about 5 but generally less than about 50 amino acids, preferably 8 to 20, and usually fewer than about 35 amino acids. In each instance, the oligopeptide will ideally be as small as possible, while still maintaining substantially all of the desired activity, e.g., blocking activity. In some instances, it may be desirable to join two or more oligopeptides from different regions, which separately or together provide the desired activities. The peptides may, of course, be fused to other proteins or molecules with desired activities (e.g., thrombolytic activity).

It will be readily appreciated by skilled artisans that the peptides employed in the subject invention need not be identical to any particular of the most preferred polypeptide sequences shown in Table 2, so long as the subject compound is able to provide blocking or other desired activities at a sufficient level. Therefore, the peptides may be subject to various changes, such as insertions, deletions, substitutions, either conservative or non-conservative, to provide for certain advantages in their use. Conservative substitutions are typically within groups, such as Gly, Ala; Val, Ile, Leu; Asp, Glu; Asn, Gln; Ser, Thr; Lys, Arg; Phe, Tyr; and Nor (norleucine), MET. Usually, the final sequence will not differ by more than about 10 to 40 percent from the naturally-occurring receptor sequence, except e.g., where additional amino acids may be added at either terminus for other utilities, including conjugation to carriers.

The peptide in which amino acid sequence has been modified by the substitution, addition or deletion of amino acid residues should retain substantially all of the blocking activity of the unmodified peptides, which may be conveniently measured by various assay techniques disclosed herein. Also, the small d-isomer form of one or more of the amino acids may be used, as desired, to modify biological properties, such as activity, rate of breakdown, etc.

Other modifications to the peptides can include the addition of one, two or more amino acids to the termini, such as to provide facilitated linking capability or to further modify the oligopeptide's physical or chemical properties. Amino acids such as tyrosine, cysteine, lysine, glutamic or aspartic acid, or the like, may be introduced at the C- or N-terminus of the oligopeptide. Cysteine is particularly preferred to facilitate covalent coupling to other peptides, to form polymers by oxidation or to form internal bridges within the oligopeptide.

Additionally, the oligopeptide sequences may differ from the natural sequences by modification according to a variety of well known biochemical reactions, such as amino-terminus acylation, e.g., acetylation, thioglycolic acid amidation, terminal-carboxy amidation (such as with ammonia or methylamine) to provide stability, increased hydrophobicity or for polymerization.

The oligopeptides of the present invention can be prepared in a wide variety of ways. The peptides, because of their relatively short size, may be synthesized in solution or on a solid support in accordance with conventional techniques. See, for example, Stuart and Young, *Solid Phase Peptide Synthesis*, 2d Edition, Pierce Chemical Co. (1984); and Tam, et al., *J. Am. Chem. Soc.* 105:6442 (1983). Various automatic synthesizers are commercially available and can be used in accordance with known protocols. Also, specialty peptides can be ordered from a variety of commercial sources such as Bio Search, Inc., San Rafael, Calif., or Peninsula Laboratories.

Alternatively, hybrid DNA technology may be employed, where a synthetic gene is prepared utilizing single DNA strands coding for the desired oligopeptides, or substantially complementary strands thereof. Where the single strands overlap, they can be brought together in an annealing medium for hybridization. The hybridized strands may then be ligated to form the complete gene, and, by choice of appropriate termini, the gene may be inserted into expression vectors. See, for example, Maniatis, et al., *Molecular Cloning, A Laboratory Manual,* Cold Spring Harbor Laboratory (1982), which is incorporated herein by reference.

As desired, fragments from the naturally occurring sequence may be employed for expression of the peptide fragments, and conservative base changes can be incorporated, such that the modified codons code for the same amino acid. Similarly, non-conservative changes can be incorporated where the resulting amino acid sequence is to be changed as discussed previously.

The coding sequence may be extended at either of the 5'- or 3'-terminus, or both termini, to extend the peptide, while retaining its blocking sites. The extension may provide for an arm for linking, e.g., to a label, such as an enzyme, for joining two or more peptides together in the same chain, for providing antigenic activity, convenient restriction sites for cloning, or the like.

The DNA sequences or fragments thereof are typically placed in expression vectors for ultimate transfection into a suitable host. See, Winnacker, E., *From Genes to Clones*, VCH Publishers, New York (1987), which is incorporated herein by reference. The host can be cultivated to enhance expression of the desired polypeptides, which then may be purified in accordance with standard techniques.

It is not known whether the subject polypeptides occur naturally. The present invention, thus, relates particularly to the non-naturally-occurring forms of receptor fragments, such as in isolated or purified, or substantially pure form. Typically, the peptides will be in a substantially different environment than in the naturally-occurring state, for example, in admixture with pharmaceutical carriers or the like. The synthetically or recombinantly produced peptides and their salts are preferred forms.

Suitable salts of the peptides according to the present invention are pharmaceutically acceptable non-toxic salts. The peptides can form acid addition salts, for example with inorganic acids, especially mineral acids. For peptides having at least one carboxy group and at least one basic group, for example an amino group, internal salts can be formed. Also, for peptides containing at least one free carboxy group, especially those having more carboxy groups than basic groups, metal ammonium salts, such as alkyline metal and alkyline earth metal salts, can be produced. Of course, for isolation and purification one may utilize pharmaceutically unsuitable salts, but only the pharmaceutically acceptable non-toxic salts should be employed for therapeutic use.

A "therapeutically effective dose" of the oligopeptides of the present invention will be an amount sufficient to diminish platelet aggregation below a level associated with pathological events, such as platelet ischemic syndromes, and yet allow adequate hemostasis. If desired, the oligopeptides may be a co-administered with other agents, such as heparin, aspirin, dipyridamole, tissue plasminogen activator, streptokinase, urokinase, sulfinpyrazone, suloctidil, the peptide Arg-Gly-Asp-Ser, and/or antibodies reactive with the IIb/IIIa receptor. See, e.g., Harker, L., *Am. J. Cardiol.*, 60:208–288 (1987), which is incorporated herein by reference.

By way of example and not limitation, the inhibition of platelet activities by interfering with the binding of fibrinogen to the IIb/IIIa receptor may find use in a wide variety of therapeutic settings, such as the following:

A. Prevention or abortion of the arterial thrombus formation

In addition to treatment of unstable angina and arterial emboli or thrombosis, the oligopeptides are useful in the treatment or prevention of myocardial infarction (MI) and mural thrombus formation post MI. For brain-related disorders, treatment or prevention of transient ischemic attack and treatment of thrombotic stroke or stroke-in-evolution are included.

B. Prevention of platelet aggregation, embolization or consumption in extracorporeal circulations These uses include improving renal dialysis, cardiopulmonary bypasses, hemoperfusions, and plasmapheresis.

C. Prevention of platelet aggregation, embolization, or consumption associated with intravascular devices Improved utility of intraaortic balloon pumps, ventricular assist devices, and arterial catheters also results.

D. Treatment or prevention of venous thrombosis

The oligopeptides will also be useful in deep venous thrombosis; IVC, renal vein, or portal vein thrombosis; and pulmonary embolism.

E. Hematologic applications

Various disorders involving platelet consumption, such as thrombotic thrombocytopenic purpura are treatable.

In addition, the peptides of the present invention may be used in numerous non-therapeutic applications where inhibiting platelet aggregation is desired. For example, improved platelet and whole blood storage can be obtained by adding sufficient quantities of the peptides, the amount of which will vary depending upon, inter alia, the length of proposed storage time, the conditions of storage, the ultimate use of the stored material, etc.

The peptide dosage can range broadly depending upon the desired affects and the therapeutic setting. Typically, dosages will be between about 0.01 and 10 milligrams per kilogram, preferably between about 0.01 to 0.1 milligrams per kilogram, body weight. Administration is preferably parenteral, such as intravenous on a daily basis for up to a week or as much as one to two months or more, all of which will vary with the peptide's size. If the peptides are sufficiently small (e.g., less than about 8–10 amino acid residues) other routes of administration can be utilized, such as intranasally, sublingually, or the like.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of non-toxic auxiliary substances, such as wetting agents, pH buffering agents, and the like. If desired, absorption enhancing preparations (e.g., liposomes) may be utilized.

Suitable in vitro assays for determining the peptides' blocking capability can be performed using standard methods (see, Gartner and Bennett, *J. Biol. Chem.*, 260:11891–11894 (1985), which is incorporated herein by reference). Platelets are first isolated from healthy human donors, preferably by gel filtration to avoid subjecting cells to the rigors of centrifugation. Purified fibrinogen and calcium are added to the gel-filtered platelets, which are then placed in an aggregometer for platelet aggregation measurements (see, Ingerman-Wojenski and Silver, *Thromb. Haemstas.*, 51:154–156 (1984) and Glazier, *Am. Clin. Prod. Dev.* (April 1987), both of which are incorporated herein by reference). Utilizing standard platelet aggregation stimuli, such as thrombin, ADP, collagen or epinephrine, the synthetic peptides are added, and aggregation inhibition measured. Thereafter, positive testing peptides are tested directly for the ability to inhibit fibrinogen binding to platelet receptor. In the subsequent assay, fibrinogen is purified from human plasma using standard technology, and labelled (e.g., with $I^{125}$). The binding of fibrinogen to the stimulated platelets is then determined (see, Bennett, et al., *J. Clin. Invest.*, 64:1393–1401 (1979), which is incorporated herein by reference).

When the peptides of the present invention are polymerized to each other or conjugated to carriers, they are particularly useful for raising antibodies (polyclonal or monoclonal) against the GPIIIa portion of the receptor. Where different peptides are used in the antigenic mixture, it is possible to induce the production of antibodies immunoreactive with several epitopes of the glycoprotein.

The subject oligopeptides may be employed linked to a soluble macromolecule, typically not less than about 5 kD, carrier. Conveniently, the carrier may be a poly (amino acid), either naturally-occurring or synthetic, to which antibodies are likely to be encountered in human serum. Examples of such carriers are poly-Lysine, hemocyanin, thyroglobulin, albumins, such as bovine serum albumin, tetanus toxoid, etc. As desired, one or more different oligopeptides of the present invention may be linked to the same macromolecule.

The manner of linking the oligopeptide with the carrier is conventional, such reagents as p-maleimidobenzoic acid, p-methyldithiobenzoic acid, maleic acid anhydride, succinic acid anhydride, glutaraldehyde, etc. The linkage may occur at the N-terminus, C-terminus or at a site intermediate to the ends of the molecule. The peptide may be derivatized by linking, may be linked while bound to a solid support, or the like, to form antigens or for other uses.

Numerous methodologies are presently known in the art for producing monoclonal antibodies (MoAbs) to the peptides. See, e.g., Goding, *Monoclonal Antibodies; Principles and Practice*, Academic Press, 2d Ed. (1986), which is incorporated herein by reference. Less preferred forms of immunoglobulins may be produced by methods well known to those skilled in the art, e.g., chromatographic purification of polyclonal sera to produce substantially monospecific antibody populations.

A commonly employed process for producing MoAbs involves fusion, under appropriate conditions, of an immortalizing cell line with a B-lymphocyte which produces the desired antibody. Immortalizing cell lines are well known in the art, and include lines which are of mammalian origin, typically of murine, rat, bovine, or human origins. They are generally tumor lines or cells obtained by transforming a normal cell line with, for example, Epstein Barr virus. Any immortalizing line can be used to prepare the hybridoma of the invention.

Similarly, techniques for obtaining the appropriate lymphocytes from mammals injected with the target antigen are well understood. Generally, either peripheral blood lymphocytes and cells of human origin are desired, or spleen cells, if mammalian non-human sources are employed. A subject mammal is injected with repeated dosages of the purified antigen, and the mammal is permitted to generate the desired antibody producing spleen cells or blood lymphocytes before these are harvested for fusion with the immortalizing line.

Techniques for fusion are also well known in the art and, in general, involve mixing the cells with a fusing agent such as, most commonly, polyethylene glycol. Preparation of a hybridoma by fusing these two types of cells is, by now, well known in the art. Successful hybridoma formation is assessed and selected by standard procedures, such as, for example, HAT selection. From among successful hybridomas, those secreting the desired antibody are selected by assaying the culture medium for their presence. Ordinarily, this is done using immunoreaction based assays, including, without limitation, Western Blot, Elisa, or RIA assays. The antibodies can be recovered from the medium using standard protein purification techniques.

Antibodies reactive with the oligopeptides of the present invention will find various diagnostic uses, e.g., in detecting the presence of the GPIIb/IIIa receptor on various cell populations in accordance with techniques well-known to those skilled in the art. Further, the antibodies can serve as thrombus imaging agents, when labelled with $^{131}$I; $^{99}$Tc; and the like.

Experimentally, the following assay was used to assist in identifying peptides within the GPIIIa protein that inhibit the binding of fibrinogen to GPIIb-IIIa. Purified GPIIb-IIIa was added to the bottoms of 96-well microtiter plates. Biotinylated fibrinogen was then added, in the presence or absence of possible inhibitors of fibrinogen binding to GPIIb-IIIa, and allowed to incubate for 3 hours at 30° C. The plates were then washed, and an anti-biotin antibody conjugated to alkaline-phosphatase added. After a 30 minute incubation, the plate was again washed, and a substrate for alkaline phosphatase (p-nitrophenyl phosphate) added. The amount of fibrinogen bound to GPIIb-IIIa was quantitated by reading the optical density of each well at 405 nm.

Using this assay, the region extending from the asparagine at amino acid #203 to the alanine at amino acid #227 of the GPIIIa NH$_2$-terminus was identified as blocking. In particular, within this sequence a 12 amino acid peptide (XXIII–XXIV) was found to inhibit fibrinogen binding to GPIIb-IIIa. Moreover, a polyclonal antibody raised against both peptide XXXIII, encompassing an amino-terminal portion of peptide 203–227, inhibited fibrinogen-binding to GPIIb-IIIa in the plate assay and partially inhibited the ADP-induced aggregation of human platelets.

Without intending to be bound to a particular theory, it is believed that the above peptides are binding to fibrinogen, mimicking the binding site on GPIIIa. Evidence for this mechanism of action includes the finding that pre-incubation of fibrinogen with the peptides greatly potentiated the inhibition of fibrinogen binding to GPIIb-IIIa. Thus, after infusion, the subject peptides would bind to fibrinogen at the GPIIb-IIIa binding site, and render the coupled fibrinogen incapable of binding to activated platelets. This provides specific inhibition of platelet aggregation, which will have therapeutic benefits, as in settings such as unstable angina or immediately following angioplasty. The peptides are also extremely useful in raising antibodies capable of blocking the interaction between GPIIIa and fibrinogen.

The identification of the GPIIIa region from peptide 203 to 227 as a fibrinogen-binding domain provides a means of screening large numbers of compounds (e.g., antibodies, organics, and the like) for potential use as inhibitors of fibrinogen-binding to GPIIb-IIIa on platelets. This is accomplished by coating the bottoms of 96-well microtiter plates with one or more of peptide XXIII, peptide XXIV or the XXIII/XXIV overlap peptide, then mixing in a sample of labelled compounds (such as radiolabeled antibiotics or organic compounds) and determining which bind to the selected peptide(s). Alternatively, an antibody specific for the compound can be included to determine if the screened compound binds to the peptide(s). Compounds which are shown to bind to one or more of these peptides are then tested directly for their ability to inhibit fibrinogen binding to GPIIb-IIIa.

These peptides will also find use in determining which region of fibrinogen binds to GPIIb-IIIA. For example, the XXIII/XXIV overlap peptide is coupled to Affi-Gel 10 beads (BioRad, Richmond, Calif.) and a proteolytic digest of fibrinogen passed over the column. Fragments of fibrinogen which bind to the immobilized peptide (and not control peptides) are sequenced (from the N-terminal) to identify GPIIb-IIIa binding sites within fibrinogen. These peptides are then synthetically manufactured and examined for their ability to inhibit fibrinogen binding to GPIIb-IIIa as detailed above.

From the foregoing, it will thus be appreciated that in addition to the peptides' blocking characteristics, the peptides provide guidance on what regions of GPIIIa are important for binding to fibrinogen. Thus, structural analogs can be provided which remain blocking, but at significantly lower amounts (i.e., concentration levels). These analogs can also be designed specifically for economic production, storage and administration.

Although the present invention has been described in some detail by way of illustration for purposes of clarity of understanding, it will be apparent that certain changes and modifications may be practiced within the scope of the amended claims.

---

We claim:

1. An isolated and purified oligopeptide comprising the amino acid sequence:

Glu-Glu-Val-Lys-Lys-Gln-Ser-Val-Ser-Arg-Asn-Arg-Asp-Ala-Pro-Glu-Gly-Gly-Phe-Asp (SEQ ID NO.:9);

Asn-Glu-Glu-Val-Lys-Lys-Gln-Ser-Val-Ser-Arg-Asn-Arg-Asp-Ala-Pro-Glu-Gly-Gly-Phe-Asp-Ala-Ile-Met-Gln-Ala (SEQ ID NO.:11);

Asn-Glu-Glu-Val-Lys-Lys-Gln-Ser-Val-Ser-Arg-Asn-Arg-Asp-Ala-Pro-Glu-Gly-Gly (SEQ ID NO.:12);

Ser-Val-Ser-Arg-Asn-Arg-Asp-Ala-Pro-Glu-Gly-Gly-Phe-Asp-Ala-Ile-Met-Gln-Ala (SEQ ID NO.:13); or

Ser-Val-Ser-Arg-Asn-Arg-Asp-Ala-Pro-Glu-Gly-Gly; (SEQ ID NO.:14)

wherein the oligopeptide has less than about 50 continuous amino acids from the naturally occurring GPIIIa sequence.

2. The oligopeptide according to claim 1, wherein the oligopeptide is a salt.

3. The oligopeptide according to claim 1, wherein the carboxy-terminal amino acid of the oligopeptide is free or amidated.

4. The oligopeptide according to claim 1, wherein the amino-terminal amino acid of the oligopeptide is free or acetylated.

5. The oligopeptide according to claim 1, wherein the oligopeptide is conjugated to a carrier, and wherein the conjugate has less than about 50 continuous amino acids from the naturally occurring GPIIIa sequence.

6. The oligopeptide according to claim 5, wherein the carrier is a protein.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
Gly  Ser  Pro  Arg  Cys  Asp  Leu  Lys  Glu  Asn  Leu  Leu  Lys  Asp  Asn  Cys
1                   5                        10                       15
Ala  Pro
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

```
Ala  Arg  Val  Leu  Glu  Asp  Arg  Pro  Leu  Ser  Asp  Lys  Gly  Ser  Gly  Asp
1                   5                        10                       15
Ser  Ser  Gln  Val
              20
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

```
Arg  Leu  Arg  Pro  Asp  Asp  Ser  Lys  Asn  Phe  Ser
1                   5                        10
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown (ii) MOLECULE TYPE: peptide (xi) SEQUENCE DESCRIPTION: SEQ ID NO:4:

```
Gln Val Arg Gln Val Glu Asp Tyr Pro Val Asp
1               5                   10
```

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:5:

```
Ser Tyr Ser Met Lys Asp Asp Leu Trp Ser Ile
1               5                   10
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:6:

```
Ala Thr Gln Met Arg Lys Leu Thr Ser
1               5
```

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:7:

```
Tyr Ile Ser Pro Pro Glu Ala Leu Glu Asn Pro Cys Tyr Asp Met Lys
1               5                   10                  15
Thr Thr
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:8:

```
Asp Gln Val Thr Arg Phe Asn Glu Glu Val Lys Lys Gln Ser Val Ser
1               5                   10                  15
Arg Asn Arg Asp
                20
```

(2) INFORMATION FOR SEQ ID NO:9:

(i) SEQUENCE CHARACTERISTICS:

( A ) LENGTH: 20 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:9:

Glu Glu Val Lys Lys Gln Ser Val Ser Arg Asn Arg Asp Ala Pro Glu
1               5                   10                  15
Gly Gly Phe Asp
        20

( 2 ) INFORMATION FOR SEQ ID NO:10:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:10:

Val Cys Asp Glu Lys Ile Gly Trp Arg Asn Asp Ala Ser
1               5                   10

( 2 ) INFORMATION FOR SEQ ID NO:11:

( i ) SEQUENCE CHARACTERISTICS:
    ( A ) LENGTH: 26 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:11:

Asn Glu Glu Val Lys Lys Gln Ser Val Ser Arg Asn Arg Asp Ala Pro
1               5                   10                  15
Glu Gly Gly Phe Asp Ala Ile Met Gln Ala
        20                  25

( 2 ) INFORMATION FOR SEQ ID NO:12:

( i ) SEQUENCE CHARACTERISTICS:
    ( A ) LENGTH: 19 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:12:

Asn Glu Glu Val Lys Lys Gln Ser Val Ser Arg Asn Arg Asp Ala Pro
1               5                   10                  15
Glu Gly Gly ( 2 ) INFORMATION FOR SEQ ID NO:13:

( i ) SEQUENCE CHARACTERISTICS:
    ( A ) LENGTH: 19 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:13:

```
Ser  Val  Ser  Arg  Asn  Arg  Asp  Ala  Pro  Glu  Gly  Gly  Phe  Asp  Ala  Ile
1              5                        10                      15

Met  Gln  Ala
```

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:14:

```
Ser  Val  Ser  Arg  Asn  Arg  Asp  Ala  Pro  Glu  Gly  Gly
1              5                        10
```

( 2 ) INFORMATION FOR SEQ ID NO:15:

( i ) SEQUENCE CHARACTERISTICS:
        ( A ) LENGTH: 200 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..200
        ( D ) OTHER INFORMATION: /note="The first 200
            amino- terminal residues of GPIIIa."

( x i ) SEQUENCE DESCRIPTION: SEQ ID NO:15:

```
Gly  Pro  Asn  Ile  Cys  Thr  Thr  Arg  Gly  Val  Ser  Ser  Cys  Gln  Gln  Cys
1              5                        10                      15

Leu  Ala  Val  Ser  Pro  Met  Cys  Ala  Trp  Cys  Ser  Asp  Glu  Ala  Leu  Pro
               20                  25                       30

Leu  Gly  Ser  Pro  Arg  Cys  Asp  Leu  Lys  Glu  Asn  Leu  Leu  Lys  Asp  Asn
          35                       40                       45

Cys  Ala  Pro  Glu  Ser  Ile  Glu  Phe  Pro  Val  Ser  Glu  Ala  Arg  Val  Leu
     50                       55                  60

Glu  Asp  Arg  Pro  Leu  Ser  Asp  Lys  Gly  Ser  Gly  Asp  Ser  Ser  Gln  Val
65                       70                       75                       80

Thr  Gln  Val  Ser  Pro  Gln  Arg  Ile  Ala  Leu  Arg  Leu  Arg  Pro  Asp  Asp
                85                       90                       95

Ser  Lys  Asn  Phe  Ser  Ile  Gln  Val  Arg  Gln  Val  Glu  Asp  Tyr  Pro  Val
               100                      105                      110

Asp  Ile  Tyr  Tyr  Leu  Met  Asp  Leu  Ser  Tyr  Ser  Met  Lys  Asp  Asp  Leu
          115                      120                      125

Trp  Ser  Ile  Gln  Asn  Leu  Gly  Thr  Lys  Leu  Ala  Thr  Gln  Met  Arg  Lys
     130                      135                 140

Leu  Thr  Ser  Asn  Leu  Arg  Ile  Gly  Phe  Gly  Ala  Phe  Val  Asp  Lys  Pro
145                      150                      155                      160

Val  Ser  Pro  Tyr  Met  Tyr  Ile  Ser  Pro  Pro  Glu  Ala  Leu  Glu  Asn  Pro
               165                      170                      175

Cys  Tyr  Asp  Met  Lys  Thr  Thr  Cys  Leu  Pro  Met  Phe  Gly  Tyr  Lys  His
          180                      185                      190

Val  Leu  Thr  Leu  Thr  Asp  Gln  Val
          195                      200
```